US010272012B2

(12) United States Patent
Muhl et al.

(10) Patent No.: US 10,272,012 B2
(45) Date of Patent: Apr. 30, 2019

(54) LAY-ON VIBRATOR

(75) Inventors: Till Muhl, Hamburg (DE); Meike Hahr, Hamburg (DE); Heiko Tullney, Hamburg (DE)

(73) Assignee: OVO JOINT VENTURE LLC, Hightstown, NJ (US)

( * ) Notice: Subject to any disclaimer, the term of this patent is extended or adjusted under 35 U.S.C. 154(b) by 1039 days.

(21) Appl. No.: 14/397,841

(22) PCT Filed: Apr. 30, 2012

(86) PCT No.: PCT/EP2012/057900
§ 371 (c)(1),
(2), (4) Date: Jul. 15, 2015

(87) PCT Pub. No.: WO2013/164008
PCT Pub. Date: Nov. 7, 2013

(65) Prior Publication Data

US 2015/0313791 A1 Nov. 5, 2015

(51) Int. Cl.
*A61F 5/00* (2006.01)
*A61H 19/00* (2006.01)
*A61H 23/02* (2006.01)

(52) U.S. Cl.
CPC ............ *A61H 19/34* (2013.01); *A61H 23/02* (2013.01); *A61H 23/0263* (2013.01)

(58) Field of Classification Search
CPC ........ A61H 19/00; A61H 19/30; A61H 19/34; A61H 19/40; A61H 19/44
USPC ...................................................... 600/38–41
See application file for complete search history.

(56) References Cited

U.S. PATENT DOCUMENTS 6,685,660 B1 * 2/2004 Taverna ............ A61H 23/0263 601/133
9,717,643 B2 * 8/2017 Guang .................. A61H 19/34
2002/0068900 A1 * 6/2002 Barnes .................. A61H 19/00 604/107

* cited by examiner

*Primary Examiner* — John Lacyk
(74) *Attorney, Agent, or Firm* — Richard E. Oney; Venjuris, P.C.

(57) ABSTRACT

The invention relates to a lay-on vibrator having vibration means (10) for creating vibrations and a body (4)including said vibration means (10), characterized by a movable element (6) adapted to reciprocally pivot relative to said body (4).

12 Claims, 4 Drawing Sheets

LAY-ON VIBRATOR

The present invention relates to a lay-on vibrator having vibration means for creating vibrations and a body including said vibration means.

The lay-on vibrator is a stimulation device of a special kind which is to be brought into contact or touch with or to be laid upon the skin of a portion of a human body, wherein vibrations created by the vibration means are transferred from the body of the lay-on vibrator to the skin of said human body portion and, hence, into said human body portion in order to stimulate said human body portion. In particular, such a lay-on vibrator is used for sexual stimulation by bringing it into contact with a sexual organ like the female clitoris.

It is an object of the present invention, to improve a lay-on vibrator for achieving a better stimulation effect.

In order to achieve the above and further objects, according to the present invention, there is provided a lay-on vibrator having vibration means for creating vibrations and a body including said vibration means, characterized by a movable element adapted to reciprocally pivot relative to said body.

So, the lay-on vibrator according to the present invention comes with an extra function in order to provide an additional particular stimulation effect. This extra stimulation effect is achieved by the movable element which is additionally provided according to the present invention and adapted to reciprocally pivot relative to the body of the lay-on vibrator, so that said movable element can be used somewhat like a vibrating feather which tickles the skin of a human body portion softly, whereas the body of the lay-on vibrator including the vibration means is to be used like a conventional lay-on vibrator.

Further advantageous embodiments and modifications of the present invention are defined in the dependent claims.

According to a preferred embodiment, said movable element is formed integrally with said body of the lay-on vibrator, which allows for an easy production of the lay-on vibrator according to the present invention.

According to a further preferred embodiment, said movable element is flexible relative to the body of the lay-on vibrator. To make the movable element flexible is a rather simple constructional measure for a pivotable arrangement of said movable element. This is in particular advantageous if the movable element is formed integrally with the body of the lay-on vibrator.

According to a still further preferred embodiment, said movable element comprises a flexible, preferably flappy, end which enables the movable element according to the present invention in a very efficient way to be used somewhat like a vibrating feather softly tickling the skin of a human body portion.

In a still further preferred embodiment, said body of the lay-on vibrator comprises a vibrating portion adapted to transfer vibrations created by said vibration means, wherein said vibrating portion is spaced from said movable element. Due to the provision of a vibrating portion for transferring vibrations created by said vibration means and the arrangement of said vibrating portion in a distance from said movable element, the lay-on vibrator according to the present invention can be used with its two different functions in a very advantageous way, i.e. with the movable element according to the present invention somewhat like a vibrating feather which tickles the skin softly, and at the side of said vibrating portion as a normal lay-on vibrator.

According to an advantageous modification of the aforementioned embodiment, said body of the lay-on vibrator comprises an elongated shape having a first end portion and a second end portion opposite to said first end portion, wherein said vibrating portion defines said first end portion and said movable element is provided at said second end portion. So, the lay-on vibrator according to this modification of the present invention can be used at its first end portion like a normal lay-on vibrator to be brought into touch with a human body portion and at its second end portion like a vibrating feather softly tickling the skin of a human body portion.

According to a further advantageous modification of the aforementioned embodiment, the vibrating portion has a rounded shape which defines a round side of the lay-on vibrator to be used like a normal lay-on vibrator.

Further, said vibrating portion may comprise a hard surface which is very suitable to achieve efficient vibration transfer and in particular a maximum vibration transfer.

According to a still further advantageous modification of the aforementioned embodiment, said vibration means comprises a drive means and an excenter rotatably driven by said drive means, wherein said excenter is provided in said vibrating portion. The use of an excenter and its arrangement in said vibrating portion lead to the creation and transferring of rather strong vibrations.

According to a still further advantageous modification of the aforementioned embodiment, said movable element is reciprocally driven by said drive means, too. So, in this modification, said drive means is not only used for rotatably driving the aforementioned excenter, but also at the same time for driving said movable element so as to reciprocally pivot relative to the body of the lay-on vibrator. Consequently, in this modification, only one single drive means is used for driving the excenter and the movable element so that the size of the lay-on vibrator can be kept small.

In a still further advantageous modification of the aforementioned embodiment, the body of the lay-on vibrator includes a chargeable battery for providing said vibration means with electrical power, wherein said vibrating portion is provided with an electrical connector coupled to said battery and adapted to be connected with an external charging device. So, additionally said vibrating portion is advantageously used for accommodation of an electrical connector provided for connection of an electrical cable so as to charge the battery by means of an external charging device.

According to a still further modification of the aforementioned embodiment, a button for switching on or off said vibration means is provided at said vibrating portion. The arrangement of such a switching on/off button at said vibrating portion has the advantage that the provision of such a button does not disturb the function of said movable element, but said movable is kept clear from the provision of such a button.

Preferably, the body of the lay-on vibrator comprises a curved shape having a concave side and a convex side opposite to said concave side. Such a shape not only gives the lay-on vibrator an elegant form, but also has the advantage that the lay-on vibrator may better fit to human body portions which often have a rounded or bent shape.

According to an advantageous modification of the aforementioned embodiment, said button is provided at the convex side of said body of the lay-on vibrator since the convex side offers a good access of said button.

In the following, a preferred embodiment according to the present invention will be described with reference to the accompanying drawings in which.

In the FIGS. 1 to 5, there is shown a lay-on vibrator 2 according to a preferred embodiment of the present invention. The lay-on vibrator 2 comprises an elongated body 4 having a rounded end portion 4*a*. The body 4 comprises a curved shape having a convex outer side 4*b* and an inner side 4*c* opposite to the outer side 4*b*.

As further shown in the figures, the lay-on vibrator 2 comprises a movable element 6 which is provided at a portion of the body 4 distant from its rounded end portion 4*a* and, in the shown embodiment, is formed integrally with the body 4. The movable element 6 is flexible relative to the body 4 and, hence, adapted to reciprocally pivot relative to the body 4. Further, the movable element comprises a flexible flappy end 6*a*. The surface of at least a part of the body 4 and/or the movable element 6 is preferably made of silicone.

Figure 4:
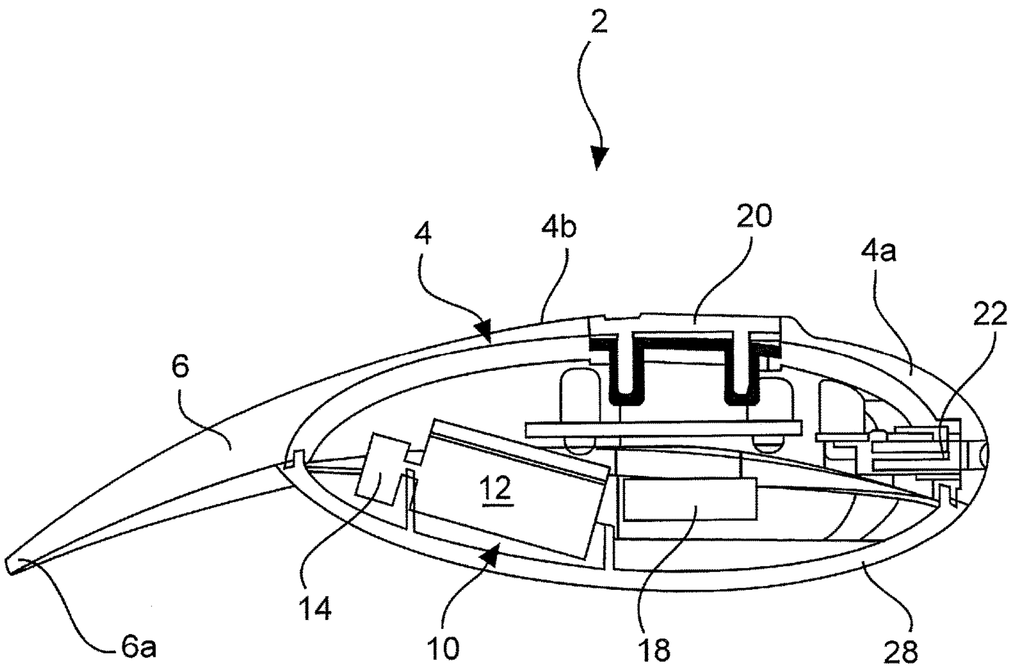
FIG. 4 is a schematic lengthwise cross-section view of the lay-on vibrator of FIG. 1 further showing the vibration means included in the body of the lay-on vibrator.

As schematically shown lines in FIG. 4, the body 4 includes a vibration means 10 which, in the shown embodiment, comprises an electrical motor 12 and an excenter 14 driven by the motor 12 and placed adjacent to the movable element 6. Vibrations created by the rotation of the excenter 14 are transferred through the rounded end portion 4*a* in order to achieve a vibration of the body 4 of the lay-on vibrator 2 at its rounded end portion 4*a*. For a maximum vibration transfer, the rounded end portion 4*a* and in particular the whole body 4 is provided with a hard surface. Since due to the operation of the excenter 14 the rounded end portion 4*a* is subject to strong vibrations, the rounded end portion 4*a* can also be called a vibrating portion. Moreover, the excenter 14 is is provided to cause the movable element 6 to reciprocally pivot or oscillate relative to the body 4.

Figure 1:
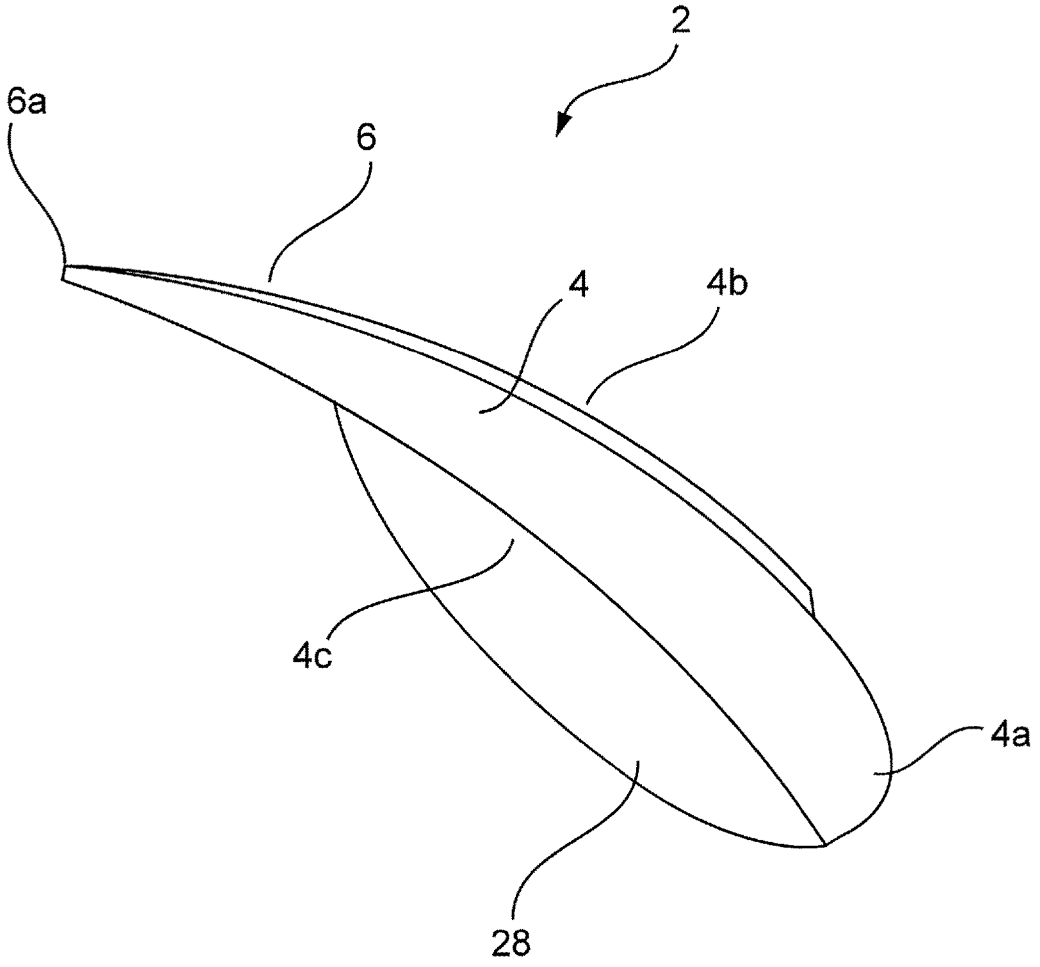
FIG. 1 is a perspective side view of a lay-on vibrator according to a preferred embodiment of the present invention.
Figure 2:
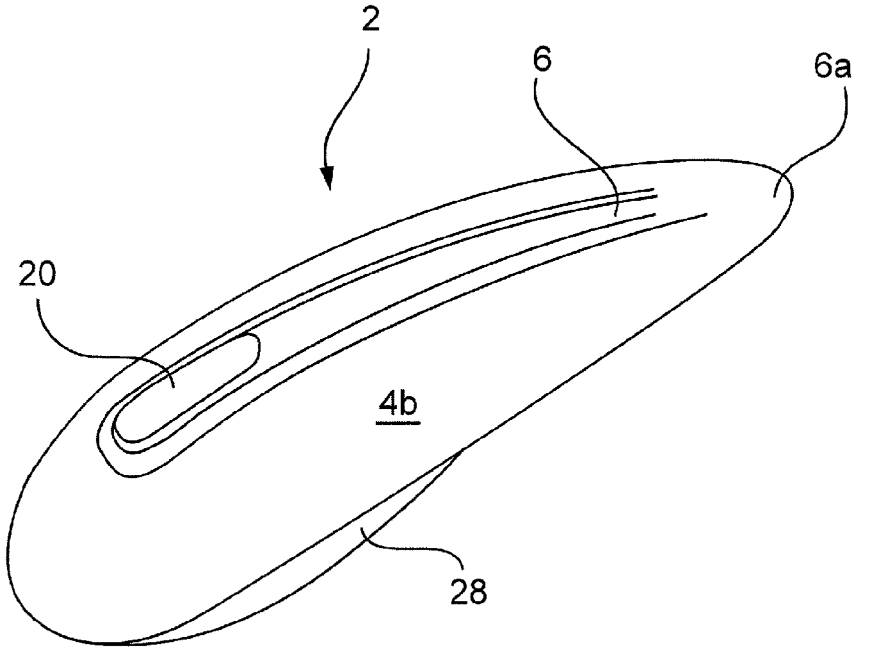
FIG. 2 is a perspective view of the lay-on vibrator of FIG. 1 from the above.
Figure 3:
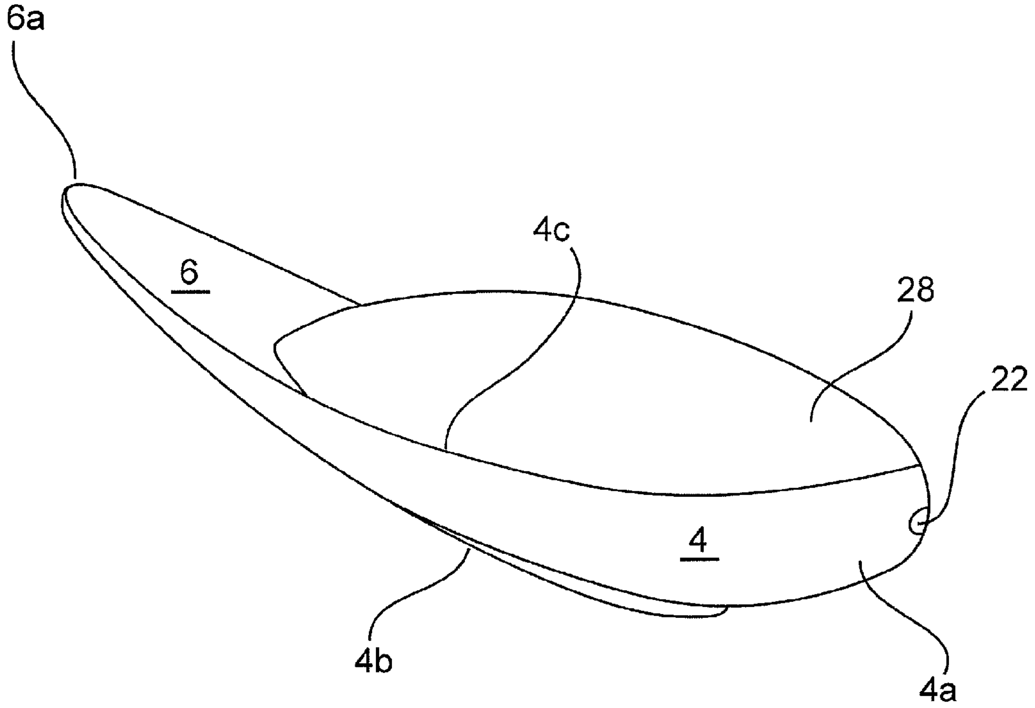
FIG. 3 is a perspective bottom view of the lay-on vibrator of FIG. 1.
Figure 5:
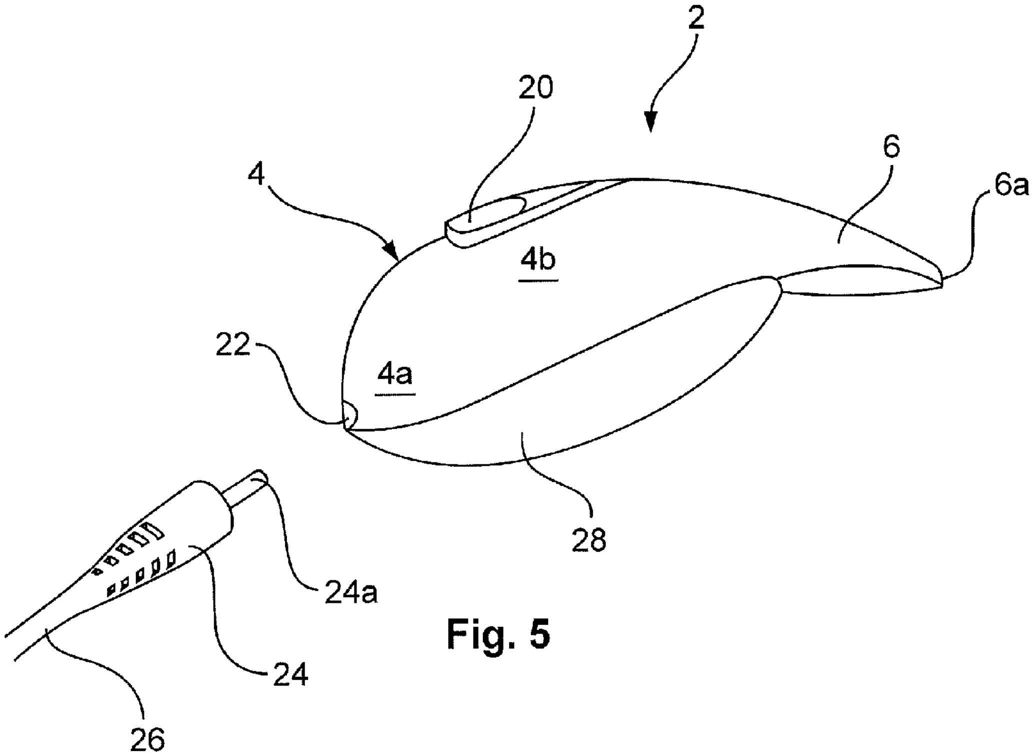
FIG. 5 is another perspective side view of the lay-on vibrator of FIG. 1, wherein a part of a cable and an electrical plug coupled to the cable are additionally shown.

For supplying the vibration means 10 with electrical power, there is provided a chargeable battery 18 which is located within the body 4 of the lay-on vibrator 2, too, as further shown in FIG. 4. For activating or deactivating the vibration means 10, there is further provided an on/off button 20 which, in the shown embodiment, is placed on the convex outer surface 4*b* of the body 4 adjacent to or within the region of the rounded end portion 4*a*, as shown in the FIGS. 2, 4 and 5. The battery 18 is connected to an electrical socket 22 provided at the rounded end portion 4*a* of the body 4. The socket 22 which is shown in the FIGS. 3, 4 and 5 is adapted to accommodate a lug jack 24*a* of an electrical plug 24 coupled with a cable 26 as shown in FIG. 5 in order to connect the chargeable battery 18 (as shown in dotted lines in FIG. 1) to an external electrical charging device (not shown) for charging. FIG. 5 shows the electrical plug 24 with its cable 26 disconnected from the socket 22.

In the shown embodiment, a further elongated body 28 is provided at the inner side 4*c* of the body 4. This further body 28 extends about along the length of the elongated body 4 from its rounded end portion 4*a* up to a location where the movable element 6 is arranged to the body 4. As shown in FIG. 4, this additional body 28 is provided to essentially accommodate the vibration means 10 and the battery 18. So, both the bodies 4 and 28 form a common casing for accommodating the vibration means 10, the battery 18, the on/off button 20, the socket 22 and further components not shown. As further seen from the figures, this additional body 28 has a convex shape.

Figure 6:
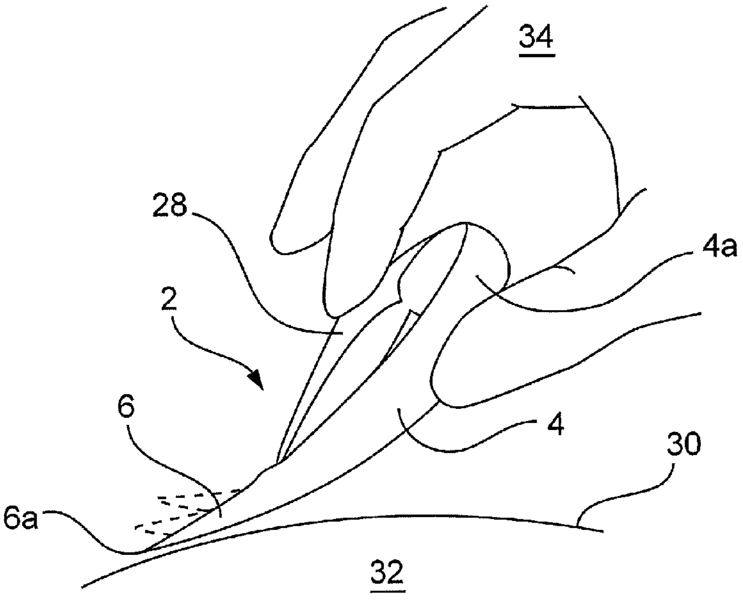
FIG. 6 is a side view of the lay-on vibrator of FIG. 1 during use.

FIG. 6 schematically shows the described lay-on vibrator 2 during use. Since the movable element 6 is adapted to reciprocally pivot or oscillate relative to the body 4 of the lay-on vibrator 2, its flexible flappy end 6*a* can be used as a vibrating feather which tickles the skin 30 of a human body portion 32 softly. During this action of the lay-on vibrator 2, as shown in FIG. 56 the lay-on vibrator 2 is gripped by a hand 34 of a user in the region of the rounded end portion 4*a* of the body. For a better illustration of the oscillating movement of the flexible flappy end 6*a* of the movable element 6, FIG. 6 schematically as an example shows the movable element 6 with its flexible flappy end 6*a* in three different pivot positions two of which are shown in dotted lines.

Whereas FIG. 6 schematically shows the use of the lay-on vibrator 2 for tickling the skin 30 of a human body portion 32 by the oscillating movable element 6, the lay-on vibrator 2 can be alternatively used at the side of the rounded end portion 4*a* of its body 4 as a conventional lay-on vibrator. For this function, the lay-on vibrator 2 is gripped at the movable element 6 by the hand 34 of a user and is to be brought into contact with the skin 30 of a human body portion 32 at the rounded end portion 4*a* of its body 4 so that at the side of the rounded end portion 4*a* of the body 4 the lay-on vibrator 2 is used in a conventional way. So, the lay-on vibrator 2 according to the above described embodiment can be used in two different ways, i.e. (1.) with the movable element 6 somewhat like a vibrating feather which tickles the skin 30 softly according to the illustration of FIGS. 6, and (2.) at the side of the rounded end portion 4*a* of the body 4 as a normal lay-on vibrator.

The invention claimed is:

1. A lay-on vibrator comprising:

vibration means for creating vibrations;

a vibrator body having an elongated shape with a first end and an opposing second end;

wherein the vibrator body includes a vibrating portion adapted to transfer vibrations created by the vibration means to the skin of a user to provide stimulation;

wherein the vibrating portion includes a rounded shape at the first end of the vibrator body and wherein a movable element is provided at the second end of the vibrator body; and wherein the movable element is adapted to reciprocally move relative to the vibrator body, the reciprocal movement providing an additional stimulation effect.

2. The lay-on vibrator according to claim 1, wherein the movable element is formed integrally with the vibrator body.

3. The lay-on vibrator according to claim 1, wherein the movable element is flexible.

4. The lay-on vibrator according to claim 1, wherein the movable element comprises a flexible end.

5. The lay-on vibrator according to claim 1, wherein the vibrating portion comprises a hard surface.

6. The lay-on vibrator according to claim 1, wherein the vibration means comprises an excenter disposed within the vibrating portion and a drive means for rotatably driving the excenter.

7. The lay-on vibrator according to claim 6, wherein the movable element is reciprocally driven by the drive means.

8. The lay-on vibrator according, to claim 1, wherein the vibrator body includes a chargeable battery for providing the vibration means with electrical power, wherein the vibrating portion is provided with an electrical connector coupled to the battery and adapted to be connected with an external charging device.

9. The lay-on vibrator according to claim 1, wherein a button for switching on or off the vibration means is provided at the vibrating portion.

10. The lay-on vibrator according to claim 1, wherein the vibrator body comprises a curved shape having a concave side and a convex side opposite to the concave side.

11. The lay-on vibrator according to claim 9, wherein the vibrator body comprises a curved shape having a concave side and a convex side-opposite to the concave side and the button is provided at the convex side of the vibrator body.

12. The lay-on vibrator according to claim 1, wherein the material of a surface of at least a part of the vibrator body or the movable element comprises silicone.

* * * * *